United States Patent
Rudnic et al.

(10) Patent No.: US 6,730,320 B2
(45) Date of Patent: May 4, 2004

(54) TETRACYCLINE ANTIBIOTIC PRODUCT, USE AND FORMULATION THEREOF

(75) Inventors: Edward M. Rudnic, N. Potomac, MD (US); James D. Isbister, Potomac, MD (US); Donald J. Treacy, Jr., Arnold, MD (US); Sandra E. Wassink, Frederick, MD (US)

(73) Assignee: Advancis Pharmaceutical Corp., Germantown, MD (US)

( * ) Notice: Subject to any disclaimer, the term of this patent is extended or adjusted under 35 U.S.C. 154(b) by 175 days.

(21) Appl. No.: 10/028,590

(22) Filed: Dec. 20, 2001

(65) Prior Publication Data

US 2002/0136766 A1 Sep. 26, 2002

Related U.S. Application Data

(63) Continuation-in-part of application No. 09/792,092, filed on Feb. 22, 2001, which is a continuation-in-part of application No. 09/687,229, filed on Oct. 13, 2000.
(60) Provisional application No. 60/184,546, filed on Feb. 24, 2000.

(51) Int. Cl.$^7$ .............................. A61K 9/00; A61K 9/20; A61K 9/22; A61K 9/54; A61K 9/14
(52) U.S. Cl. ...................... 424/468; 424/400; 424/457; 424/464; 424/471; 424/472; 424/484; 424/489; 514/964
(58) Field of Search .................... 424/400, 451, 424/452, 457, 458, 459, 463, 464, 465, 468, 469, 471, 472, 474, 478, 484, 489; 514/962, 963, 964, 965

(56) References Cited

U.S. PATENT DOCUMENTS

| | | | |
|---|---|---|---|
| 4,435,173 A | 3/1984 | Siposs et al. ................. 609/155 |
| 4,616,008 A | 10/1986 | Hirai et al. .................. 514/200 |
| 4,794,001 A | 12/1988 | Mehta et al. ................. 424/458 |
| 4,831,025 A | 5/1989 | Godtfredsen et al. ......... 514/195 |
| 4,904,476 A | 2/1990 | Mehta et al. ................. 424/456 |
| 4,915,953 A | 4/1990 | Jordan et al. ................ 424/473 |
| 4,971,805 A | 11/1990 | Kitanishi et al. ............. 424/494 |
| 5,011,692 A | 4/1991 | Fujioka et al. ............... 424/426 |
| 5,110,597 A | 5/1992 | Wong et al. .................. 424/438 |
| 5,213,808 A | 5/1993 | Bar-Shalom et al. ......... 424/473 |
| 5,229,131 A | 7/1993 | Amidon et al. .............. 424/451 |
| 5,395,626 A | 3/1995 | Kotwal et al. ............... 424/472 |
| 5,401,512 A | 3/1995 | Rhodes et al. ............... 424/458 |
| 5,413,777 A * | 5/1995 | Sheth et al. ................. 424/490 |
| 5,414,014 A | 5/1995 | Schneider et al. ........... 514/535 |
| 5,445,829 A | 8/1995 | Paradissis et al. ........... 424/480 |
| 5,462,747 A | 10/1995 | Radebaugh et al. .......... 424/465 |
| 5,472,708 A | 12/1995 | Chen .......................... 424/451 |
| 5,508,040 A | 4/1996 | Chen .......................... 424/451 |
| 5,538,954 A * | 7/1996 | Koch et al. ................... 514/53 |
| 5,567,441 A | 10/1996 | Chen .......................... 424/494 |
| 5,672,359 A | 9/1997 | Digenis et al. .............. 424/463 |
| 5,719,132 A | 2/1998 | Lin et al. ...................... 514/50 |
| 5,827,531 A | 10/1998 | Morrison et al. ............ 424/450 |
| 5,840,329 A | 11/1998 | Bai .............................. 424/458 |
| 5,877,243 A | 3/1999 | Sarangapani ................ 524/139 |
| 5,883,079 A * | 3/1999 | Zopf et al. .................... 514/25 |
| 5,910,322 A | 6/1999 | Rivett et al. ................. 424/484 |
| 6,027,748 A | 2/2000 | Conte et al. ................. 424/458 |
| 6,120,803 A * | 9/2000 | Wong et al. .................. 424/473 |
| 6,132,771 A | 10/2000 | Depui et al. ................. 424/468 |
| 6,294,199 B1 | 9/2001 | Conley et al. ............... 424/468 |
| 6,358,525 B1 | 3/2002 | Guo et al. .................... 424/464 |
| 2001/0046984 A1 | 11/2001 | Rudnic et al. .......... 514/210.09 |
| 2001/0048944 A1 | 12/2001 | Rudnic et al. ............... 424/468 |
| 2002/0004070 A1 | 1/2002 | Rudnic et al. ............... 424/468 |
| 2002/0004499 A1 | 1/2002 | Rudnic et al. ............... 514/192 |

FOREIGN PATENT DOCUMENTS

| | | |
|---|---|---|
| WO | WO 94/27557 | 12/1994 |
| WO | WO 95/20946 | 8/1995 |
| WO | WO 96/04908 | 2/1996 |
| WO | WO 98/22091 | 5/1998 |

\* cited by examiner

*Primary Examiner*—Thurman K. Page
*Assistant Examiner*—Sharmila Gollamudi
(74) *Attorney, Agent, or Firm*—Elliot M. Olstein; Raymond E. Stauffer

(57) ABSTRACT

An antibiotic product, in particular a tetracycline, such as doxycycline, is comprised of at least three dosages forms, each of which has a different release profile, with the $C_{max}$ for the antibiotic product being reached in less than about twelve hours. In one embodiment, there is an immediate release dosage form, as well as two or more delayed release dosage forms, with each of the dosage forms having a different release profile, wherein each reaches a $C_{max}$ at different times.

40 Claims, No Drawings

TETRACYCLINE ANTIBIOTIC PRODUCT, USE AND FORMULATION THEREOF

This application is a continuation-in-part of U.S. application Ser. No. 09/792,092, filed on Feb. 22, 2001, which is a continuation-in-part of U.S. application Ser. No. 09/687,229, filed on Oct. 13, 2000, and also claims the priority of U.S. Provisional Application Serial No. 60/184,546 filed on Feb. 24, 2000.

This invention relates to an antibiotic product, as well as the use and formulation thereof. The invention further relates to a tetracycline antibiotic product and in particular doxycycline and its derivatives, salts, hydrates, esters, metabolites, etc.

A wide variety of antibiotics have been used, and will be used, in order to combat bacterial infection. In general, such antibiotics can be administered by a repeated dosing of immediate release dosage forms, which results in poor compliance or as a controlled release formulation (slow release) at higher administered doses. The present invention is directed to providing for an improved antibiotic product.

In accordance with one aspect of the present invention, there is provided an antibiotic pharmaceutical product which is comprised of at least two, preferably at least three, antibiotic dosage forms. Such dosage forms are formulated so that each of the dosage forms has a different release profile.

In a particularly preferred embodiment, there are at least two, preferably at least three dosage forms, each of which has a different release profile and the release profile of each of the dosage forms is such that the dosage forms each start release of the antibiotic contained therein at different times after administration of the antibiotic product.

Thus, in accordance with an aspect of the present invention, there is provided a single or unitary antibiotic product that has contained therein at least two, preferably at least three antibiotic dosage forms, each of which has a different release profile, whereby the antibiotic contained in each of such dosage forms is released at different times.

In accordance with a further aspect of the invention, the antibiotic product may be comprised of at least four different dosage forms, each of which starts to release the antibiotic contained therein at different times after administration of the antibiotic product.

The antibiotic product generally does not include more than five dosage forms with different release times.

In accordance with a preferred embodiment, the antibiotic product has an overall release profile such that when administered the maximum serum concentration of the total antibiotic released from the product is reached in less than twelve hours, preferably in less than eleven hours. In an embodiment, the maximum serum concentration of the total antibiotic released from the antibiotic product is achieved no earlier than four hours after administration.

In accordance with one preferred embodiment of the inventions there are at least three dosage forms. One of the at least three dosage forms is an immediate release dosage form whereby initiation of release of the antibiotic therefrom is not substantially delayed after administration of the antibiotic product. The second and third of the at least three dosage forms is a delayed dosage form (which may be a pH sensitive or a non-pH sensitive delayed dosage form, depending on the type of antibiotic product), whereby the antibiotic released therefrom is delayed until after initiation of release of the antibiotic from the immediate release dosage form. More particularly, the antibiotic release from the second of the at least two dosage forms achieves a $C_{max}$ (maximum serum concentration in the serum) at a time after the antibiotic released from the first of the at least three dosage forms achieves a $C_{max}$ in the serum, and the antibiotic released from the third dosage form achieves a $C_{max}$ in the serum after the $C_{max}$ of antibiotic released from the second dosage form.

In one embodiment, the second of the at least two dosage forms initiates release of the antibiotic contained therein at least one hour after the first dosage form, with the initiation of the release therefrom generally occurring no more than six hours after initiation of release of antibiotic from the first dosage form of the at least three dosage forms.

In general, the immediate release dosage form produces a $C_{max}$ for the antibiotic released therefrom within from about 0.5 to about 2 hours, with the second dosage form of the at least three dosage forms producing a $C_{max}$ for the antibiotic released therefrom in no more than about four hours. In general, the $C_{max}$ for such second dosage form is achieved no earlier than two hours after administration of the antibiotic product; however, it is possible within the scope of the invention to achieve $C_{max}$ in a shorter period of time.

As hereinabove indicated, the antibiotic product may contain at least three or at least four or more different dosage forms. For example, if the antibiotic product includes a third dosage form, the antibiotic released therefrom reaches a $C_{max}$ at a time later than the $C_{max}$ is achieved for the antibiotic released from each of the first and second dosage forms. In a preferred embodiment, release of antibiotic from the third dosage form is started after initiation of release of antibiotic from both the first dosage form and the second dosage form. In one embodiment, $C_{max}$ for antibiotic release from the third dosage form is achieved within eight hours.

In another embodiment, the antibiotic product contains at least four dosage forms, with each of the at least four dosage forms having different release profiles, whereby the antibiotic release from each of the at least four different dosage forms achieves a $C_{max}$ at a different time.

As hereinabove indicated, in a preferred embodiment, irrespective of whether the antibiotic contains at least two or at least three or at least four different dosage forms each with a different release profile, $C_{max}$ for all the antibiotic released from the antibiotic product is achieved in less than twelve hours, and more generally is achieved in less than eleven hours.

In a preferred embodiment, the antibiotic product is a once a day product, whereby after administration of the antibiotic product, no further product is administered during the day; i.e., the preferred regimen is that the product is administered only once over a twenty-four hour period. Thus, in accordance with the present invention, there is a single administration of an antibiotic product with the antibiotic being released in a manner such that overall antibiotic release is effected with different release profiles in a manner such that the overall $C_{max}$ a for the antibiotic product is reached in less than twelve hours. The term single administration means that the total antibiotic administered over a twenty-four hour period is administered at the same time, which can be a single tablet or capsule or two or more thereof, provided that they are administered at essentially the same time.

Applicant has found that a single dosage antibiotic product comprised of at least three antibiotic dosage forms each having a different release profile is an improvement over a single dosage antibiotic product comprised of an antibiotic dosage form having a single release profile. Each of the dosage forms of antibiotic in a pharmaceutically acceptable carrier may have one or more antibiotics and each of the dosage forms may have the same antibiotic or different antibiotics.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antibiotic may occur. Such "leakage" is not "release" as used herein.

If at least four dosage forms are used, the fourth of the at least four dosage form may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, antibiotic release from such fourth dosage form may be initiated prior to or after release from the second or third dosage form.

The antibiotic product of the present invention, as hereinabove described, may be formulated for administration by a variety of routes of administration. For example, the antibiotic product may be formulated in a way that is suitable for topical administration; administration in the eye or the ear; rectal or vaginal administration; as nose drops; by inhalation; as an injectable; or for oral administration. In a preferred embodiment, the antibiotic product is formulated in a manner such that it is suitable for oral administration.

For example, in formulating the antibiotic product for topical administration, such as by application to the skin, the at least two different dosage forms, each of which contains an antibiotic, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide an antibiotic product in the form of a patch, which includes antibiotic dosage forms having different release profiles, as hereinabove described.

In addition, the antibiotic product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the antibiotic product with at least three different dosage forms with different release profiles may be formulated for rectal or vaginal administration, as known in the art. This may take the form of a cream or emulsion, or other dissolvable dosage form similar to those used for topical administration.

As a further embodiment, the antibiotic product may be formulated for use in inhalation therapy by coating the particles and micronizing the particles for inhalation.

In a preferred embodiment, the antibiotic product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antibiotic product. Thus, for example, antibiotic products may include a first dosage form in the form of a tablet that is an immediate release tablet, and may also include two or more additional tablets, each of which provides for a delayed release of the antibiotic, as hereinabove described, whereby the $C_{max}$ of the antibiotic released from each of the tablets is reached at different times, with the $C_{max}$ of the total antibiotic released from the antibiotic product being achieved in less than twelve hours.

The formulation of an antibiotic product including at least three dosage forms with different release profiles for different routes of administration is deemed to be within the skill of the art from the teachings herein. As known in the art, with respect to delayed release, the time of release can be controlled by the concentration of antibiotics in the coating and/or the thickness of the coating.

In formulating an antibiotic product in accordance with the invention, in one embodiment, the immediate release dosage form of the product generally provides from about 20% to about 50% of the total dosage of antibiotic to be delivered by the product, with such immediate release dosage forms generally providing at least 25% of the total dosage of the antibiotic to be delivered by the product. In many cases, the immediate release dosage form provides from about 20% to about 30% of the total dosage of antibiotic to be delivered by the product; however, in some cases it may be desirable to have the immediate release dosage form provide for about 45% to about 50% of the total dosage of antibiotic to be delivered by the product.

The remaining dosage forms deliver the remainder of the antibiotic. If more than one delayed release dosage form is used, in one embodiment, each of the delayed release dosage forms may provide about equal amounts of antibiotic; however, they may also be formulated so as to provide different amounts.

In accordance with the present invention, each of the dosage forms contains the same antibiotic; however, each of the dosage forms may contain more than one antibiotic.

In one embodiment, where the composition contains one immediate release component and two delayed release components, the immediate release component provides from 20% to 35% (preferably 20% to 30%), by weight, of the total antibiotic; where there is three delayed release components, the immediate release component provides from 15% to 30%, by weight, of the total antibiotic; and where there are four delayed release components, the immediate release component provides from 10% to 25%, by weight, of the total antibiotic.

With respect to the delayed release components, where there are two delayed release components, the first delayed release component (the one released earlier in time) provides from 30% to 60%, by weight, of the total antibiotic provided by the two delayed release components with the second delayed release component providing the remainder of the antibiotic.

Where there are three delayed release components, the earliest released component provides 20% to 35% by weight of the total antibiotic provided by the three delayed release components, the next in time delayed release component provides from 20% to 40%, by weight, of the antibiotic provided by the three delayed release components and the last in time providing the remainder of the antibiotic provided by the three delayed release components.

When there are four delayed release components, the earliest delayed release component provides from 15% to 30%, by weight, the next in time delayed release component provides from 15% to 30%, the next in time delayed release component provides from 20% to 35%, by weight, and the last in time delayed release component provides from 20% to 35%, by weight, in each case of the total antibiotic provided by the four delayed release components.

The Immediate Release Component

The immediate release portion of this system can be a mixture of ingredients that breaks down quickly after administration to release the antibiotic. This can take the form of either a discrete pellet or granule that is mixed in with, or compressed with, the other three components.

The materials to be added to the antibiotics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000–10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05–15% (W/W).

The non-pH Sensitive Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5–25% (W/W) of this component.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4–20% (W/W).

Sustained Release Component

The components in this composition are the same as the immediate release component, but with additional polymers integrated into the composition, or as coatings over the pellet or granule.

The kind of materials useful for this purpose can be, but are not limited to, ethylcellulose, hydroxypropylmethylcellulose, hydroxypropylcellulose, hydroxyethylcellulose, carboxymethylcellulose, methylcellulose, nitrocellulose, Eudragit R, and Eudragit RL, Carbopol, or polyethylene glycols with molecular weights in excess of 8,000 daltons.

These materials can be present in concentrations from 4–20% (W/W).

As hereinabove indicated, the units comprising the antibiotic composition of the present invention can be in the form of discrete pellets or particles contained in the capsule, or particles embedded in a tablet or suspended in a liquid suspension.

The antibiotic composition of the present invention may be administered, for example, by any of the following routes of administration: sublingual, transmucosal, transdermal, parenteral, etc., and preferably is administered orally. The composition includes a therapeutically effective amount of the antibiotic, which amount will vary with the antibiotic to be used, the disease or infection to be treated, and the number of times that the composition is to be delivered in a day. The composition is administered to a host in an amount effective for treating a bacterial infection.

This system will be especially useful in extending the practical therapeutic activity for antibiotics with elimination half lives of less than 20 hours and more particularly with elimination half-lives of less than 12 hours, and will be particularly useful for those drugs with half-lives of 2–10 hours. The following are examples of some antibiotics with half-lives of about 1 to 12 hours: Cefadroxil, cefazolin, cephalexin, cephalothin, cephapirin, cephacelor, cephprozil, cephadrine, cefamandole, cefonicid, ceforanide, cefuroxime, cefixime, cefoperazone, cefotaxime, cefpodoxime, ceftaxidime, ceftibuten, ceftizoxime, ceftriaxone, cefepime, cefmetazole, cefotetan, cefoxitin, loracarbef, imipenem, erythromycin (and erythromycin salts such as estolate, ethylsuccinate, gluceptate, lactobionate, stearate), azithromycin, clarithromycoin, dirithromycin, troleanomycin, penicillin V, peniciliin salts, and complexes, methicillin, nafcillin, oxacillin, cloxacillin, dicloxacillin, amoxicillin, amoxicillin and clavulanate potassium, ampicillin, bacampicillin, carbenicillin indanyl sodium (and other salts of carbenicillin) mezlocillin, piperacillin, piperacillin and taxobactam, ticarcillin, ticarcillin and clavulanate potassium, clindamycin, vancomycin, novobiocin, aminosalicylic acid, capreomycin, cycloserine, ethambutol HCl and other salts, ethionamide, and isoniazid, ciprofloxacin, levofloxacin, lomefloxacin, nalidixic acid, norfloxacin, ofloxacin, sparfloxacin, sulfacytine, suflamerazine, sulfamethazine, sulfamethixole, sulfasalazine, sulfisoxazole, sulfapyrizine, sulfadiazine, sulfmethoxazole, sulfapyridine, metronidazole, methenamine, fosfomycin, nitrofurantoin, trimethoprim, clofazimine, co-triamoxazole, pentamidine, and trimetrexate.

The invention will be further described with respect to the following examples; however, the scope of the invention is not limited thereby. All percentages in this specification, unless otherwise specified, are by weight.

EXAMPLES

Immediate Release Component

Formulate the composition by mixing the ingredients in a suitable pharmaceutical mixer or granulator such as a planetary mixer, high-shear granulator, fluid bed granulator, or extruder, in the presence of water or other solvent, or in a dry blend. If water or other solvent was used, dry the blend in a suitable pharmaceutical drier, such as a vacuum over or forced-air oven. The product may be sieved or granulated, and compressed using a suitable tablet press, such as a rotary tablet press.

| Ingredient | Conc. (% W/W) |
|---|---|
| Example 1: | |
| Amoxicillin | 65% (W/W) |
| Microcrystalline cellulose | 20 |
| Povidone | 10 |
| Croscarmellose sodium | 5 |
| Example 2: | |
| Amoxicillin | 55% (W/W) |
| Microcrystalline cellulose | 25 |
| Povidone | 10 |
| Croscarmellose sodium | 10 |
| Example 3: | |
| Amoxicillin | 65% (W/W) |
| Microcrystalline cellulose | 20 |
| Hydroxypropylcellulose | 10 |
| Croscarmellose sodium | 5 |
| Example 4: | |
| Amoxicillin | 75% (W/W) |
| Polyethylene glycol 4000 | 10 |
| Polyethylene glycol 2000 | 10 |
| Hydroxypropylcellulose | 5 |
| Example 5: | |
| Amoxicillin | 75% (W/W) |
| Polyethylene glycol 8000 | 20 |
| Polyvinylpyrrolidone | 5 |
| Example 6: | |
| Clarithromycin | 65% (W/W) |
| Microcrystalline cellulose | 20 |
| Hydroxypropylcellulose | 10 |
| Croscarmellose sodium | 5 |
| Example 7: | |
| Clarithromycin | 75% (W/W) |
| Microcrystalline cellulose | 15 |
| Hydroxypropylcellulose | 5 |
| Croscarmellose sodium | 5 |
| Example 8: | |
| Clarithromycin | 75% (W/W) |
| Polyethylene glycol 4000 | 10 |
| Polyethylene glycol 2000 | 10 |
| Hydroxypropylcellulose | 5 |
| Example 9: | |
| Clarithromycin | 75% (W/W) |
| Polyethylene glycol 8000 | 20 |
| Polyvinylpyrrolidone | 5 |
| Example 10: | |
| Ciprofloxacin | 65% (W/W) |
| Microcrystalline cellulose | 20 |
| Hydroxypropylcellulose | 10 |
| Croscarmellose sodium | 5 |
| Example 11: | |
| Ciprofloxacin | 75% (W/W) |
| Microcrystalline cellulose | 15 |
| Hydroxypropylcellulose | 5 |
| Croscarmellose sodium | 5 |
| Example 12: | |
| Ciprofloxacin | 75% (W/W) |
| Polyethylene glycol 4000 | 10 |

-continued

| Ingredient | Conc. (% W/W) |
|---|---|
| Polyethylene glycol 2000 | 10 |
| Hydroxypropylcellulose | 5 |
| Example 13: | |
| Ciprofloxacin | 75% (W/W) |
| Polyethylene glycol 8000 | 20 |
| Polyvinylpyrrolidone | 5 |
| Example 14: | |
| Ceftibuten | 75% (W/W) |
| Polyethylene glycol 4000 | 10 |
| Polyethylene glycol 2000 | 10 |
| Hydroxypropylcellulose | 5 |
| Example 15: | |
| Ceftibuten | 75% (W/W) |
| Polyethylene Glycol 4000 | 20 |
| Polyvinylpyrrolidone | 5 | non-pH Sensitive Delayed Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| Ingredient | Conc. (% W/W) |
|---|---|
| Example 16: | |
| Amoxicillin | 65% (W/W) |
| Microcrystalline cellulose | 20 |
| Polyox | 10 |
| Croscarmellose sodium | 5 |
| Example 17: | |
| Amoxicillin | 55% (W/W) |
| Microcrystalline cellulose | 25 |
| Polyox | 10 |
| Glyceryl monooleate | 10 |
| Example 18: | |
| Amoxicillin | 65% (W/W) |
| Polyox | 20 |
| Hydroxypropylcellulose | 10 |
| Croscarmellose sodium | 5 |
| Example 19: | |
| Clarithromycin | 70% (W/W) |
| Polyox | 20 |
| Hydroxypropylcellulose | 5 |
| Croscarmellose sodium | 5 |

Enteric Release Component

Formulate the ingredients by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| Ingredient | Conc. (% W/W) |
|---|---|
| *Example 20:* | |
| Amoxicillin | 65% (W/W) |
| Microcrystalline cellulose | 20 |
| Cellulose Acetate Pthalate | 15 |
| *Example 21:* | |
| Amoxicillin | 55% (W/W) |
| Microcrystalline cellulose | 25 |
| Cellulose Acetate Pthalate | 10 |
| Hydroxypropylmethylcellulose | 10 |
| *Example 22:* | |
| Amoxicillin | 65% (W/W) |
| Polyox | 20 |
| Hydroxypropylcellulose pthalate | 10 |
| Eudragit L30D | 5 |
| *Example 23:* | |
| Amoxicillin | 40% (W/W) |
| Microcrystalline Cellulose | 40 |
| Cellulose Acetate Pthalate | 10 |
| *Example 24:* | |
| Clarithromycin | 70% (W/W) |
| Hydroxypropylcellulose pthalate | 15 |
| Croscarmellose sodium | 10 |
| *Example 25:* | |
| Clarithromycin | 75% (W/W) |
| Polyethylene glycol 2000 | 10 |
| Eudragit E 30D | 15 |
| *Example 26:* | |
| Clarithromycin | 40% (W/W) |
| Lactose | 50 |
| Eudgragit L 30D | 10 |
| *Example 27:* | |
| Ciprofloxacin | 65% (W/W) |
| Microcrystalline Cellulose | 20 |
| Eudragit L 30D | 10 |
| *Example 28:* | |
| Ciprofloxacin | 75% (W/W) |
| Microcrystalline Cellulose | 15 |
| Hydroxypropylcellulose pthalate | 10 |
| *Example 29:* | |
| Ciprofloxacin | 80% (W/W) |
| Lactose | 10 |
| Eudgragit L 30D | 10 |
| *Example 30:* | |
| Ciprofloxacin | 70% (W/W) |
| Polyethylene glycol 4000 | 20 |
| Cellulose acetate pthalate | 10 |
| *Example 31:* | |
| Ceftibuten | 60% (W/W) |
| Polyethylene glycol 2000 | 10 |
| Lactose | 20 |
| Eudragit L 30D | 10 |
| *Example 32:* | |
| Ceftibuten | 70% (W/W) |
| Microcrystalline cellulose | 20 |
| Cellulose acetate pthalate | 10 |

Sustained Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| Ingredient | Conc. (% W/W) |
|---|---|
| *Example 33:* | |
| Amoxicillin | 65% (W/W) |
| Ethylcellulose | 20 |
| Polyox | 10 |
| Hydroxypropylmethylcellulose | 5 |
| *Example 34:* | |
| Amoxicillin | 55% (W/W) |
| Lactose | 25 |
| Polyox | 10 |
| Glyceryl monooleate | 10 |
| *Example 35:* | |
| Amoxicillin | 70% (W/W) |
| Polyox | 20 |
| Hydroxypropylcellulose | 10 |
| *Example 36:* | |
| Clarithromycin | 75% (W/W) |
| Lactose | 15 |
| Hydroxypropylcellulosee | 5 |
| Ethylcellulose | 5 |
| *Example 37:* | |
| Clarithromycin | 75% (W/W) |
| Polyethylene glycol 4000 | 10 |
| Lactose | 10 |
| Eudragit RL 30D | 5 |
| *Example 38:* | |
| Clarithromycin | 80% (W/W) |
| Polyethylene glycol 8000 | 10 |
| Hydroxypropylmethylcellulose | 5 |
| Eudgragit RS 30D | 5 |
| *Example 39:* | |
| Ciprofloxacin | 75% (W/W) |
| Hydroxyethylcellulose | 10 |
| Polyethylene glycol 4000 | 10 |
| Hydroxypropylcellulose | 5 |
| *Example 40:* | |
| Ciprofloxacin | 75% (W/W) |
| Lactose | 10 |
| Povidone (PVP) | 10 |
| Polyethylene glycol 2000 | 5 |
| *Example 41:* | |
| Ceftibuten | 75% (W/W) |
| Polyethylene glycol 4000 | 10 |
| Povidone (PVP) | 10 |
| Hydroxypropylcellulose | 5 |
| *Example 42:* | |
| Ceftibuten | 75% (W/W) |
| Lactose | 15 |
| Polyethylene glycol 4000 | 5 |
| Polyvinylpyrrolidone | 5 |

Three Pulses

Example 43

1. Metronidazole Matrix Pellet Formulation and Preparation Procedure (Immediate Release)

A. Pellet Formulation

The composition of the metronidazole matrix pellets provided in Table 1.

TABLE 1

Composition of Metronidazole Pellets

| Component | Percentage (%) |
| --- | --- |
| Metronidazole | 50 |
| Avicel PH 101 | 20 |
| Lactose | 20 |
| PVP K29/32* | 10 |
| Purified Water | |
| Total | 100 |

*PVP K29/32 was added as a 20% w/w aqueous solution during wet massing.

B. Preparation Procedure for Metronidazole Matrix Pellets 1.2.1 Blend metronidazole and Avicel® PH 101 using a Robot Coupe high shear granulator.
1.2.2 Add 20% Povidone K29/32 binder solution slowly into the powder blend under continuous mixing.
1.2.3 Extrude the wet mass using an LCI Bench Top Granulator. The diameter of the screen of the Bench Top Granulator was 1.0 mm.
1.2.4 Spheronize the extrudate using a Model SPH20 Caleva Spheronizer.
1.2.5 Dry the spheronized pellets at 50° C. overnight.
1.2.6 Pellets between 16 and 30 Mesh were collected for further processing.

1.3 Preparation of an Eudragit® L 30 D-55 Aqueous Coating Dispersion

A. Dispersion Formulation

The composition of the aqueous Eudragit L30D-55 dispersion applied to the metronidazole matrix pellets is provided below in Table 2.

TABLE 2

Eudragit ® L 30 D-55 Aqueous Coating Dispersion

| Component | Percentage (%) |
| --- | --- |
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

B. Preparation Procedure for an Eudragit® L 30 D-55 Aqueous Dispersion 1.3.1 Suspend triethyl citrate and talc in deionized water.
1.3.2 The TEC/talc suspension is then homogenized using a PowerGen 700 high shear mixer.
1.3.3 Add the TEC/talc suspension slowly to the Eudragit® L 30 D-55 latex dispersion while stirring.
1.3.4 Allow the coating dispersion to stir for one hour prior to application onto the metronidazole matrix pellets.

1.4 Preparation of an Eudragit® S 100 Aqueous Coating Dispersion

A. Dispersion Formulation

The composition of the aqueous Eudragit® S 100 dispersion applied to the metronidazole matrix pellets is provided below in Table 3.

TABLE 3

Eudragit ® S 100 Aqueous Coating Dispersion

| Component | Percentage (%) |
| --- | --- |
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

B. Preparation Procedure for an Eudragit® S 100 Aqueous Dispersion Part I:

(i) Dispense Eudragit® S 100 powder in deionized water with stirring.
(ii) Add ammonium hydroxide solution drop-wise into the dispersion with stirring.
(iii) Allow the partially neutralized dispersion to stir for 60 minutes.
(iv) Add triethyl citrate drop-wise into the dispersion with stirring. Stir for about 2 hours prior to the addition of Part B.

Part II:
(i) Disperse talc in the required amount of water
(ii) Homogenize the dispersion using a PowerGen 700D high shear mixer.
(iii) Part B is then added slowly to the polymer dispersion in Part A with a mild stirring.

1.5 Coating Conditions for the Application of Aqueous Coating Dispersions

The following coating parameters were used to coat matrix pellets with each of the Eudragit® L 30 D-55 and Eudragit® S100 aqueous film coating.

| | |
| --- | --- |
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

(i) Coat matrix pellets with L30 D-55 dispersion such that you apply 12% coat weight gain to the pellets.
(ii) Coat matrix pellets with S100 dispersion such that you apply 20% coat weight gain to the pellets.

1.6 Encapsulation of the Metronidazole Pellets

Pellets are filled into size 00 hard gelatin capsules at a ratio of 30%:30%:40%: Immediate-release matrix pellets uncoated, L30 D-55 coated pellets and S100 coated pellets respectively.

The capsule is filled with the three different pellets to achieve a total dose of 375 mg/capsule.

Three Pulses

Example 44

Amoxicillin Pellet Formulation and Preparation Procedure 44.1 Pellet Formulations for subsequent coating The composition of the Amoxicillin trihydrate matrix pellets provided in Table 4.

TABLE 4

Composition of Amoxicillin Matrix Pellets

| Component | Percentage (%) |
|---|---|
| Amoxicillin Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

44.2 Preparation Procedure for Amoxicillin Matrix Pellets 44.2.1 Blend Amoxicillin and Avicel® PH 101 using a low shear blender.

44.2.2 Add the hydroxypropyl methylcellulose binder solution slowly into the powder blend under continuous mixing.

44.2.3 Extrude the wet mass using an LCI Bench Top Granulator. The diameter of the screen of the Bench Top Granulator is 0.8 mm.

44.2.4 Spheronize the extrudate using a QJ-230 Spheronizer using a small cross section plate.

44.2.5 Dry the spheronized pellets at 60° C. using a fluid bed dryer until the exhaust temperature reaches 40° C.

44.2.6 Pellets between 20 and 40 Mesh were collected for further processing.

44.3 Preparation of an Eudragit® L 30 D-55 Aqueous Coating Dispersion 44.3.1 Dispersion Formulation The composition of the aqueous Eudragit L30D-55 dispersion applied to the amoxicillin matrix pellets is provided below in Table 5.

TABLE 5

Eudragit ® L 30 D-55 Aqueous Coating Dispersion

| Component | Percentage (%) |
|---|---|
| Eudragit ® L 30 D-55 | 41.6 |
| Triethyl Citrate | 2.5 |
| Talc | 5.0 |
| Purified Water | 50.9 |
| Solids Content | 20.0 |
| Polymer Content | 12.5 |

44.4 Preparation Procedure for an Eudragit® L 30 D-55 Aqueous Dispersion 44.4.1 Suspend triethyl citrate and talc in deionized water.

44.4.2 The TEC/talc suspension is mixed using laboratory mixer.

44.4.3 Add the TEC/taic suspension from slowly to the Eudragit® L 30 D-55 latex dispersion while stirring.

44.4.4 Allow the coating dispersion to stir for one hour prior to application onto the amoxicillin matrix pellets.

44.5 Preparation of an Eudragit® S 100 Aqueous Coating Dispersion 44.5.1 Dispersion Formulation The composition of the aqueous Eudragit® S 100 dispersion applied to the Amoxicillin matrix pellets is provided below in Table 6.

TABLE 6

Eudragit ® S 100 Aqueous Coating Dispersion

| Component | Percentage (%) |
|---|---|
| Part A | |
| Eudragit ® S 100 | 10.0 |
| 1 N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

44.6 Preparation Procedure for an Eudragit® S 100 Aqueous Dispersion

Part A:

44.6.1 Dispense Eudragit® S 100 powder in deionized water with stirring.

44.6.2 Add ammonium hydroxide solution drop-wise into the dispersion with stirring.

44.6.3 Allow the partially neutralized dispersion to stir for 60 minutes.

44.6.4 Add triethyl citrate drop-wise into the dispersion with stirring and let stir overnight prior to the addition of Part B.

Part B:

44.6.5 Disperse talc in the required amount of water 44.6.6 Stir the dispersion using an overhead laboratory mixer.

44.6.7 Part B is then added slowly to the polymer dispersion in Part A with a mild stirring.

44.7 Coating Conditions for the Application of Aqueous Coating Dispersions

The following coating parameters were used for both the Eudragit® L 30 D-55 and Eudragit® S 100 aqueous film coating processes.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2–6 gram per minute |

44.7.1 Coat matrix pellets with L30 D-55 dispersion such that you apply 20% coat weight gain to the pellets.

44.7.2 Coat matrix pellets with S100 dispersion such that you apply 37% coat weight gain to the pellets.

44.8 Preparation of Amoxicillin Granulation (Immediate Release Component) for tabletting

TABLE 7

Composition of Amoxicillin Granulation

| Component | Percentage (%) |
|---|---|
| Amoxicillin Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

44.8.1 Blend Amoxicillin and Avicel® PH 101 using a low shear blender.
44.8.2 Add the hydroxypropyl methylcellulose binder solution slowly into the powder blend under continuous mixing.
44.8.3 Dry the granulation at 60° C. using a fluid bed dryer until the exhaust temperature reaches 40° C.
44.8.4 Granules between 20 and 40 Mesh are collected for further processing.
44.9 Tabletting of the Amoxicillin Pellets

TABLE 8

Composition of Amoxicillin Tablets

| Component | Percentage (%) |
|---|---|
| Amoxicillin granules | 32.5 |
| Avicel PH 200 | 5.0 |
| Amoxicillin L30D-55 coated pellets | 30 |
| Amoxicillin S100 coated pellets | 30 |
| Colloidal silicon dioxide | 1.5 |
| Magnesium stearate | 1.0 |
| Total | 100 |

44.9.1 Blend the Amoxicillin granules, Avicel PH-200, Amoxicillin pellets and colloidal silicon dioxide for 15 minutes in a tumble blender.
44.9.2 Add the magnesium stearate to the blender, and blend for 5 minutes.
44.9.3 Compress the blend on a rotary tablet press.
44.9.4 The fill weight should be adjusted to achieve a 500 mg dose tablet.

Three Pulses

Example 45

Clarithromycin Pellet Formulation and Preparation Procedure 45.1 Pellet Formulation The composition of the clarithromycin matrix pellets provided in Table 1.

TABLE 9

Composition of Clarithromycin Pellets

| Component | Percentage (%) |
|---|---|
| Clarithromycin | 50.6 |
| Lactose monohydrate, spray dried | 32.1 |
| Silicified microcrystalline cellulose | 14.6 |
| Polyoxyl 35 Castor Oil* | 1.7 |
| Hydroxypropyl methylcellulose* | 1.0 |
| Total | 100 |

*Hydroxypropyl methylcellulose and Polyoxyl 35 were added as an 8.7% w/w aqueous solution during wet massing.

45.2 Preparation Procedure for Clarithromycin Matrix Pellets 45.2.1 Blend clarithromycin, silicified microcrystalline cellulose and lactose monohydrate using a Robot Coupe high shear granulator.
45.2.2 Prepare the binder solution by adding the Polyoxyl to the purified water while stirring. After that is mixed, slowly add the hydroxypropyl methylcellulose and continue to stir until a solution is achieved.
45.2.3 Add binder solution slowly into the powder blend under continuous mixing.
45.2.4 Granulate the powders in the high shear granulator with the binder solution.
45.2.5 Extrude the wet mass using an LCI Bench Top Granulator. The diameter of the screen of the Bench Top Granulator was 1.2 mm.
45.2.6 Spheronize the extrudate using a Model SPH20 Caleva Spheronizer.
45.2.7 Dry the spheronized pellets at 50° C. overnight.
45.2.8 Pellets between 18 and 30 Mesh were collected for further processing.
45.3 Preparation of an Eudragit® L 30 D-55 Aqueous Coating Dispersion 45.3.1 Dispersion Formulation The composition of the aqueous Eudragit L30D-55 dispersion applied to the clarithromycin matrix pellets is provided below in Table 10.

TABLE 10

Eudragit ® L 30 D-55 Aqueous Coating Dispersion

| Component | Percentage (%) |
|---|---|
| Eudragit ® L 30 D-55 | 40.4 |
| Triethyl Citrate | 1.8 |
| Talc | 6.1 |
| Water | 51.7 |
| Solids Content | 20.0 |
| Polymer Content | 12.1 |

45.4 Preparation Procedure for an Eudragit® L 30 D-55 Aqueous Dispersion 45.4.1 Suspend triethyl citrate and talc in deionized water.
45.4.2 The TEC/talc suspension is then homogenized using a PowerGen 700 high shear mixer.
45.4.3 Add the suspension from 4.2.2 slowly to the Eudragit® L 30 D-55 latex dispersion while stirring.
45.4.4 Allow the coating dispersion to stir for one hour prior to application onto the clarithromycin matrix pellets.
45.5 Preparation of an Eudragit® S 100 Aqueous Coating Dispersion 45.5.1 Dispersion Formulation The composition of the aqueous Eudragit® S 100 dispersion applied to the clarithromycin matrix pellets is provided below in Table 11.

TABLE 11

Eudragit ® S 100 Aqueous Coating Dispersion

| Component | Percentage (%) |
|---|---|
| Part A | |
| Eudragit ® S 100 | 10.0 |
| 1 N Ammonium Hydroxide | 5.1 |
| Triethyl Citrate | 5.0 |
| Water | 64.9 |

TABLE 11-continued

Eudragit ® S 100 Aqueous Coating Dispersion

| Component | Percentage (%) |
|---|---|
| Part B | |
| Talc | 5.0 |
| Water | 10.0 |
| Solid Content | 25.0 |
| Polymer Content | 10.0 |

45.6 Preparation Procedure for an Eudragit® S 100 Aqueous Dispersion

Part A:

45.6.1 Dispense Eudragit® S 100 powder in deionized water with stirring.
45.6.2 Add ammonium hydroxide solution drop-wise into the dispersion with stirring.
45.6.3 Allow the partially neutralized dispersion to stir for 60 minutes
45.6.4 Add the triethyl citrate drop-wise to the dispersion and stir for 60 minutes prior to the addition of Part B.

Part B:

45.6.5 Disperse talc in the required amount of water
45.6.6 Homogenize the dispersion using a PowerGen 700D high shear mixer.
45.6.7 Part B is then added slowly to the polymer dispersion in Part A with a mild stirring.

45.7 Coating Conditions for the Application of Aqueous Coating Dispersions

The following coating parameters were used for coating the matrix pellets with each of the Eudragit® L 30 D-55 and Eudragit® S 100 aqueous film coating.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.6 Bar |
| Pump Rate | 2 gram per minute |

45.7.1 Coat matrix pellets with L30 D-55 dispersion such that you apply 20% coat weight gain to the pellets.
45.7.2 Coat matrix pellets with S100 dispersion such that you apply 37% coat weight gain to the pellets.
4. Capsules were filled with the uncoated pellets, the L30D-55 coated pellets and S100 coated pellets in weight percentages of 30%:30%:40%, respectively to provide 250 mg. capsules.

Four Pulses

Example 46

1 Metronidazole Matrix Pellet Formulation and Preparation Procedure 46.1 Pellet Formulation The composition of the metronidazole matrix pellets provided in Table 12.

TABLE 12

Composition of Metronidazole Pellets

| Component | Percentage (%) |
|---|---|
| Metronidazole | 50 |
| Avicel PH 101 | 20 |
| Lactose | 20 |
| PVP K29/32* | 10 |
| Purified Water | |
| Total | 100 |

*PVP K29/32 was added as a 20% w/w aqueous solution during wet massing.

46.2 Preparation Procedure for Metronidazole Matrix Pellets 46.2.1 Blend metronidazole and Avicel® PH 101 using a Robot Coupe high shear granulator.
46.2.2 Add 20% Povidone K29/32 binder solution slowly into the powder blend under continuous mixing.
46.2.3 Extrude the wet mass using an LCI Bench Top Granulator. The diameter of the screen of the Bench Top Granulator was 1.0 mm.
46.2.4 Spheronize the extrudate using a Model SPH20 Caleva Spheronizer.
46.2.5 Dry the spheronized pellets at 50° C. overnight.
46.2.6 Pellets between 16 and 30 Mesh were collected for further processing.

46.3 Preparation of an Eudragit® L 30 D-55 Aqueous Coating Dispersion 46.3.1 Dispersion Formulation The composition of the aqueous Eudragit L30D-55 dispersion applied to the metronidazole matrix pellets is provided below in Table 13.

TABLE 13

Eudragit ® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

46.4 Preparation Procedure for an Eudragit® L 30 D-55 Aqueous Dispersion 46.4.1 Suspend triethyl citrate and talc in deionized water.
46.4.2 The TEC/talc suspension is then homogenized using a PowerGen 700 high shear mixer.
46.4.3 Add the TEC/talc suspension slowly to the Eudragit® L 30 D-55 latex dispersion while stirring.
46.4.4 Allow the coating dispersion to stir for one hour prior to application onto the metronidazole matrix pellets.

46.5 Preparation of an Eudragit® S 100 Aqueous Coating Dispersion 46.5.1 Dispersion Formulation The composition of the aqueous Eudragit® S 100 dispersion applied to the metronidazole matrix pellets is provided below in Table 14.

TABLE 14

Eudragit ® S 100 Aqueous Coating Dispersion

| Component | Percentage (%) |
|---|---|
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

46.6 Preparation Procedure for an Eudragit® S 100 Aqueous Dispersion

Part A:

46.6.1 Dispense Eudragit® S 100 powder in deionized water with stirring.

46.6.2 Add ammonium hydroxide solution drop-wise into the dispersion with stirring.

46.6.3 Allow the partially neutralized dispersion to stir for 60 minutes.

46.6.4 Add triethyl citrate drop-wise into the dispersion with stirring. Stir for about 2 hours prior to the addition of Part B.

Part B:

46.6.5 Disperse talc in the required amount of water 46.6.6 Homogenize the dispersion using a PowerGen 700D high shear mixer.

46.6.7 Part B is then added slowly to the polymer dispersion in Part A with a mild stirring.

46.7 Coating Conditions for the Application of Aqueous Coating Dispersions

The following coating parameters were used for coating with each of the Eudragit® L 30 D-55 and Eudragit® S 100 aqueous film coatings.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

46.7.1 Coat matrix pellets with L30 D-55 dispersion such that you apply 12% coat weight gain to the pellets.

46.7.2 Coat matrix pellets with L30 D-55 dispersion such that you apply 30% coat weight gain to the pellets.

46.7.3 Coat matrix pellets with S100 dispersion such that you apply 20% coat weight gain to the pellets.

46.8 Encapsulation of the Metronidazole Pellets

Pellets are filled into size 00 hard gelatin capsules at a ratio of 20%:30%:20%:30% Immediate-release matrix pellets (uncoated), L30 D-55 coated pellets 12% weight gain, L30D-55 coated pellets 30% weight gain and S100 coated pellets respectively. The capsule is filled with the four different pellets to achieve a total dose of 375 mg/capsule.

Four Pulses

Example 47

Amoxicillin Pellet Formulation and Preparation Procedure 47.1 Pellet Formulations The composition of the Amoxicillin trihydrate matrix pellets provided in Table 15.

TABLE 15

Composition of Amoxicillin Matrix Pellets

| Component | Percentage (%) |
|---|---|
| Amoxicillin Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

47.2 Preparation Procedure for Amoxicillin Matrix Pellets 47.2.1 Blend Amoxicillin and Avicel® PH 101 using a low shear blender.

47.2.2 Add the hydroxypropyl methylcellulose binder solution slowly into the powder blend under continuous mixing.

47.2.3 Extrude the wet mass using an LCI Bench Top Granulator. The diameter of the screen of the Bench Top Granulator is 0.8 mm.

47.2.4 Spheronize the extrudate using a QJ-230 Spheronizer using a small cross section plate.

47.2.5 Dry the spheronized pellets at 60° C. using a fluid bed dryer until the exhaust temperature reaches 40° C.

47.2.6 Pellets between 20 and 40 Mesh were collected for further processing.

47.3 Preparation of an Eudragit® L 30 D-55 Aqueous Coating Dispersion 47.3.1 Dispersion Formulation The composition of the aqueous Eudragit L30D-55 dispersion applied to the amoxicillin matrix pellets is provided below in Table 16.

TABLE 16

Eudragit ® L 30 D-55 Aqueous Coating Dispersion

| Component | Percentage (%) |
|---|---|
| Eudragit ® L 30 D-55 | 41.6 |
| Triethyl Citrate | 2.5 |
| Talc | 5.0 |
| Purified Water | 50.9 |
| Solids Content | 20.0 |
| Polymer Content | 12.5 |

47.4 Preparation Procedure for an Eudragit® L 30 D-55 Aqueous Dispersion 47.4.1 Suspend triethyl citrate and talc in deionized water.

47.4.2 The TEC/talc suspension is mixed using laboratory mixer.

47.4.3 Add the TEC/talc suspension from slowly to the Eudragit® L 30 D-55 latex dispersion while stirring.

47.4.4 Allow the coating dispersion to stir for one hour prior to application onto the amoxicillin matrix pellets.

47.5 Preparation of an Eudragit® claim 11, wherein S 100 Aqueous Coating Dispersion 47.6 Dispersion Formulation The composition of the aqueous Eudragit® S 100 dispersion applied to the Amoxicillin matrix pellets is provided below in Table 17.

TABLE 17

Eudragit ® S 100 Aqueous Coating Dispersion

| Component | Percentage (%) |
| --- | --- |
| Part A | |
| Eudragit ® S 100 | 10.0 |
| 1 N Ammonium Hydroxide | 5.1 |
| Triethyl Citrate | 5.0 |
| Water | 64.9 |
| Part B | |
| Talc | 2.0 |
| Water | 10.0 |
| Solid Content | 25.0 |
| Polymer Content | 10.0 |

47.7 Preparation Procedure for an Eudragit® S 100 Aqueous Dispersion

Part A:

47.7.1 Dispense Eudragit® S 100 powder in deionized water with stirring.

47.7.2 Add ammonium hydroxide solution drop-wise into the dispersion with stirring.

47.7.3 Allow the partially neutralized dispersion to stir for 60 minutes.

47.7.4 Add triethyl citrate drop-wise into the dispersion with stirring and let stir overnight prior to the addition of Part B.

Part B:

47.7.5 Disperse talc in the required amount of water 47.7.6 Stir the dispersion using an overhead laboratory mixer.

47.7.7 Part B is then added slowly to the polymer dispersion in Part A with a mild stirring.

47.8 Preparation of Aquacoat Coating Dispersion 47.8.1 Dispersion Formulation

The composition of the aqueous Aquacoat dispersion applied to Amoxicillin L30 D-55 coated pellets is provided below in Table 18.

TABLE 18

| Component | Percentage (%) |
| --- | --- |
| Aquacoat ECD | 79.3 |
| Hydroxypropyl methylcellulose | 15.9 |
| Dibutyl Sebacate | 4.8 |
| Purified Water (300 g) | |

47.8.1.1 Prepare Hydroxypropyl methylcellulose (Methocel E15) solution by dispersing in water with continuous stirring.

47.8.1.2 Add Aquacoat and dibutyl sebacate to the dispersion with stirring and continue to stir overnight.

47.9 Coating Conditions for the Application of Aqueous Coating Dispersions

The following coating parameters were used for coating with each of the Eudragit® L 30 D-55 and Eudragit® S 100 aqueous film coatings.

| Coating Equipment | STREA 1 ™ Table Top Laboratory Fluid Bed Coater |
| --- | --- |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2–6 gram per minute |

47.9.1 Coat Amoxicillin matrix pellet s with L30 D-55 dispersim to achieve a 20% coat weight gain.

47.9.2 Coat another batch of Amoxicillin matrix pellets with L30 D-55 dispersion to achieve a 20% weight gain. Coat the L30 D-55 pellets with the Aquacoat Dispersion to achieve a 10% coat weight gain.

47.9.3 Coat Amoxicillin matrix pellets with S100 dispersion to achieve a 37% coat weight gain.

47.10 Preparation of Amoxicillin Granulation for Tabletting

TABLE 19

Composition of Amoxicillin Granulation (Immediate Release)

| Component | Percentage (%) |
| --- | --- |
| Amoxicillin Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

47.10.1 Blend Amoxicillin and Avicel® PH 101 using a low shear blender.

47.10.2 Add the hydroxypropyl methylcellulose binder solution slowly into the powder blend under continuous mixing.

47.10.3 Dry the granulation at 60° C. using a fluid bed dryer until the exhaust temperature reaches 40° C.

47.10.4 Granules between 20 and 40 Mesh are collected for further processing.

47.11 Tabletting of the Amoxicillin Pellets

TABLE 20

Composition of Amoxicillin Tablets

| Component | Percentage (%) |
| --- | --- |
| Amoxicillin granules | 32.5 |
| Avicel PH 200 | 5.0 |
| Amoxicillin L30D-55 coated pellets | 20 |
| Amoxicillin Aquacoated pellets | 20 |
| Amoxicillin S100 coated pellets | 20 |
| Colloidal silicon dioxide | 1.5 |
| Magnesium stearate | 1.0 |
| Total | 100 |

47.11.1 Blend the Amoxicillin granules, Avicel PH-200, Amoxicillin pellets and colloidal silicon dioxide for 15 minutes in a tumble blender.

47.11.2 Add the magnesium stearate to the blender, and blend for 5 minutes.

47.11.3 Compress the blend on a rotary tablet press.

47.11.4 The fill weight should be adjusted to achieve a 500 mg dose tablet.

Four Pulses

Example 48

Clarithromycin Pellet Formulation and Preparation Procedure 48.1 Pellet Formulation The composition of the clarithromycin matrix pellets provided in Table 21.

TABLE 21

Composition of Clarithromycin Pellets

| Component | Percentage (%) |
|---|---|
| Clarithromycin | 50.6 |
| Lactose monohydrate, spray dried | 32.1 |
| Silicified microcrystalline cellulose | 14.6 |
| Polyoxyl 35 Castor Oil* | 1.7 |
| Hydroxypropyl methylcellulose* | 1.0 |
| Total | 100 |

*Hydroxypropyl methylcellulose and Polyoxyl 35 were added as an 8.7% w/w aqueous solution during wet massing.

48.2 Preparation Procedure for Clarithromycin Matrix Pellets 48.2.1 Blend clarithromycin, silicified microcrystalline cellulose and lactose monohydrate using a Robot Coupe high shear granulator.

48.2.2 Prepare the binder solution by adding the Polyoxyl to the purified water while stirring. After that is mixed, slowly add the hydroxypropyl methylcellulose and continue to stir until a solution is achieved.

48.2.3 Add binder solution slowly into the powder blend under continuous mixing.

48.2.4 Granulate the powders in the high shear granulator with the binder solution.

48.2.5 Extrude the wet mass using an LCI Bench Top Granulator. The diameter of the screen of the Bench Top Granulator was 1.2 mm.

48.2.6 Spheronize the extrudate using a Model SPH20 Caleva Spheronizer.

48.2.7 Dry the spheronized pellets at 50° C. overnight.

48.2.8 Pellets between 18 and 30 Mesh were collected for further processing.

48.3 Preparation of an Eudragit® L 30 D-55 Aqueous Coating Dispersion 48.3.1 Dispersion Formulation The composition of the aqueous Eudragit L30D-55 dispersion applied to the clarithromycin matrix pellets is provided below in Table 22.

TABLE 22

Eudragit ® L 30 D-55 Aqueous Coating Dispersion

| Component | Percentage (%) |
|---|---|
| Eudragit ® L 30 D-55 | 40.4 |
| Triethyl Citrate | 1.8 |
| Talc | 6.1 |
| Water | 51.7 |
| Solids Content | 20.0 |
| Polymer Content | 12.1 |

48.4 Preparation Procedure for an Eudragit® L 30 D-55 Aqueous Dispersion 48.4.1 Suspend triethyl citrate and talc in deionized water.

48.4.2 The TEC/talc suspension is then homogenized using a PowerGen 700 high shear mixer.

48.4.3 Add the suspension from 4.2.2 slowly to the Eudragit® L 30 D-55 latex dispersion while stirring.

48.4.4 Allow the coating dispersion to stir for one hour prior to application onto the clarithromycin matrix pellets.

48.5 Preparation of an Eudragit® S 100 Aqueous Coating Dispersion 48.5.1 Dispersion Formulation The composition of the aqueous Eudragit® S 100 dispersion applied to the clarithromycin matrix pellets is provided below in Table 23.

TABLE 23

Eudragit ® S 100 Aqueous Coating Dispersion

| Component | Percentage (%) |
|---|---|
| Part A | |
| Eudragit ® S 100 | 10.0 |
| 1 N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

48.6 Preparation Procedure for an Eudragit® S 100 Aqueous Dispersion

Part A:

48.6.1 Dispense Eudragit® S 100 powder in deionized water with stirring.

48.6.2 Add ammonium hydroxide solution drop-wise into the dispersion with stirring.

48.6.3 Allow the partially neutralized dispersion to stir for 60 minutes 48.6.4 Add the triethyl citrate drop-wise to the dispersion and stir for 60 minutes prior to the addition of Part B.

Part B:

48.6.5 Disperse talc in the required amount of water 48.6.6 Homogenize the dispersion using a PowerGen 700D high shear mixer.

48.6.7 Part B is then added slowly to the polymer dispersion in Part A with a mild stirring.

48.7 Coating Conditions for the Application of Aqueous Coating Dispersions

The following coating parameters were used for coating with each of the Eudragit® L 30 D-55 and Eudragit® S 100 aqueous film coatings.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.6 Bar |
| Pump Rate | 2 gram per minute |

48.7.1 Coat matrix pellets with L30 D-55 dispersion such that you apply 12% coat weight gain to the pellets.

48.7.2 Coat matrix pellets with L30 D-55 dispersion such that you apply 30% coat weight gain to the pellets.

48.7.3 Coat matrix pellets with S100 dispersion such that you apply 37% coat weight gain to the pellets.

48.8 Encapsulation of the Clarithromycin Pellets

Pellets are filled into size 00 hard gelatin capsules at a ratio of 20%:30%:20%:30% Immediate-release matrix pellets (uncoated), L30 D-55 coated pellets 12% weight gain, L30D-55 coated pellets 30% weight gain and S100 coated pellets respectively. The capsule is filled with the four different pellets to achieve a total dose of 250 mg/capsule.

Four Pulses

Example 49

Doxycycline Hyclate Pellet Formulation and Preparation Procedure

Pellet Formulation

The composition of the Doxycycline hyclate pellets provided in Table 24.

TABLE 24

Composition of Doxycycline hyclate Pellets

| Component | Percentage (%) |
|---|---|
| Doxycycline hyclate | 93 |
| Avicel PH 101 | 3 |
| Methocel E5P LV | 4 |
| Purified Water | * |
| Total | 100 |

*Removed during processing

Preparation Procedure for Doxycycline Hyclate Pellets

Blend Doxycycline hyclate, Avicel® PH 101, and Methocel using a Robot Coupe high shear granulator.

Add the purified water slowly into the powder blend under continuous mixing.

Extrude the wet mass using an LCI Bench Top Granulator. The diameter of the screen of the Bench Top Granulator was 1.0 mm.

Spheronize the extrudate using a Model SPH20 Caleva Spheronizer.

Dry the spheronized pellets at 50° C. until moisture level is <3%.

Pellets between 16 and 30 Mesh were collected for further processing.

Doxycycline Hyclate Enteric-Release Pellet Formulation and Preparation Procedure Preparation of an Eudragit® L 30 D-55/Eudragit NE 30D Aqueous Coating Dispersion Dispersion Formulation The composition of the aqueous Eudragit L30D-55/Eudragit NE 30D aqueous coating dispersion applied to the doxycycline hyclate pellets is provided below in Table 25.

TABLE 25

Eudragit ® L 30 D-55/Eudragit NE 30D Aqueous Coating Dispersion

| Component | Percentage (%) |
|---|---|
| Eudragit ® L 30D-55 | 44.4 |
| Eudragit NE 30D | 14.8 |
| Triethyl Citrate | 1.3 |
| Imwitor 900 | 0.9 |
| Purified Water* | 38.6 |
| Solid Content | 20.6 |
| Polymer Content | 16.4 |

*Removed during processing

Preparation Procedure for an Eudragit® L 30D-55/Eudragit NE 30D Aqueous Dispersion Heat purified water to 75–80° C. and then add triethyl citrate (TEC) and Imwitor 900. Homogenize dispersion until temperature is less than 55° C.

The TEC/Imwitor 900 dispersion is then stirred until the temperature is less than 35° C.

Add the TEC/Imwitor 900 dispersion to Eudragit L30D-55 latex dispersion and stir for at least 30 minutes.

Add Eudragit NE 30D to the Eudragit L30D/TEC/Imwitor 900 dispersion and stir for at least 10 minutes.

Screen the dispersion through a No. 60 mesh sieve prior to coating.

Continue to stir the dispersion until the coating process is complete.

Coating Conditions for the Application of Eudragit L30D-55/Eudragit NE 30D Agueous Coating Dispersion The following coating parameters were used for coating of the Eudragit® L 30 D-55/Eudragit NE30D film coating dispersion.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 45° C. |
| Outlet Air Temperature | 32 to 35° C. |
| Atomization Air Pressure | 1.6 Bar |
| Pump Rate | 3–4 gram per minute |

Coat doxycycline hyclate pellets with Eudragit L30 D-55/Eudragit NE 30D film coating dispersion such that you apply 20% coat weight gain to the pellets.

Doxycycline hyclate Delayed Enteric-Release Pellet Formulation and Preparation Procedure Preparation of an Opadry Clear Coating Solution Dispersion Formulation The composition of the aqueous Opadry solution applied to the Doxycycline hyclate pellets is provided below in Table 26.

TABLE 26

Opadry Clear Aqueous Coating Solution

| Component | Percentage (%) |
|---|---|
| Opadry Clear YS-1-7006 | 7.0 |
| Purified Water* | 93.0 |
| Solid Content % | 7.0 |
| Polymer Content % | 7.0 |

*Removed during processing

Preparation Procedure for Opadry Clear Aqueous Solution

Charge the purified water into a container

Slowly add the Opadry Clear YS-1-7006 to the water with continuous mixing.

Preparation of an Eudragit® FS 30D/Eudragit L 30D-55 Aqueous Coating Dispersion

Dispersion Formulation

The composition of the aqueous Eudragit FS 30D/Eudragit L 30D-55 coating dispersion applied to the Opadry coated Doxycycline hyclate pellets is provided below in Table 27.

TABLE 27

AQOAT AS-HF/Eudragit FS 30D Coating Dispersion

| Component | Percentage (%) |
|---|---|
| Eudragit L 30D-55 | 5.8 |
| Eudagit FS 30D | 17.5 |
| Triethyl Citrate | 1.3 |
| Talc | 1.4 |
| Purified Water* | 74.0 |
| Solid Content | 9.7 |
| Polymer Content | 7.0 |

*Removed during processing

Preparation Procedure for Eudragit FS 30D/Eudragit L 30D-55 Aqueous Dispersion

Disperse triethyl citrate in purified water with stirring.

Slowly add talc into the triethyl citrate dispersion with stirring.

Slowly add the Eudragit L 30D-55 to the dispersion above and stir for a minimum of 10 minutes.

Slowly add the Eudragit FS 30D dispersion to the Eudragit L 30D-55 dispersion and continue to stir for a minimum of 1 hour.

Screen the dispersion through a No. 60 mesh sieve.

Continue to stir the screened coating dispersion throughout the coating process.

Coating Conditions for the Application of Opadry and Eudragit FS 30D/Eudragit L 30D-55 Aqueous Coating Dispersions The following coating parameters were used for coating with the Opadry solution film coating.

| Coating Equipment | STREA 1 ™ Table Top Laboratory Fluid Bed Coater |
|---|---|
| Spray nozzle diameter | 1.0 mm |
| Material Charge | 350 gram |
| Inlet Air Temperature | 60° C. |
| Outlet Air Temperature | 40° C. |
| Atomization Air Pressure | 1.6 Bar |

Coat Doxycycline hyclate pellets with Opadry coating solution such that you apply 3% coat weight gain to the pellets.

The following coating parameters were used for coating with the Eudragit FS 30D/Eudragit L30D-55 film coating dispersion.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 50° C. |
| Outlet Air Temperature | 30° C. |
| Atomization Air Pressure | 1.6 Bar |

Coat Opadry coated Doxycycline hyclate pellets with the Eudragit FS30D/Eudragit L 30D-55 coating dispersion such that you apply 20% coat weight gain to the pellets.

Doxycycline Hyclate Colonic-Release Pellet Formulation and Preparation Procedure Preparation of an Eudragit® FS30D Aqueous Coating Dispersion Dispersion Formulation The composition of the aqueous Eudragit® FS 30D dispersion applied to the doxycycline hyclate pellets is provided below in Table 28.

TABLE 28

| Eudragit ® FS 30D Aqueous Coating Dispersion | |
|---|---|
| Component | Percentage (%) |
| Eudragit ® FS 30D | 54.8 |
| Triethyl Citrate | 0.9 |
| Talc | 3.3 |
| Purified Water* | 41.0 |

TABLE 28-continued

| Eudragit ® FS 30D Aqueous Coating Dispersion | |
|---|---|
| Component | Percentage (%) |
| Solid Content | 20.6 |
| Polymer Content | 16.4 |

*Removed during processing

Preparation Procedure for an Eudragit® FS 30D Aqueous Disipersion

Disperse triethyl citrate (TEC) in the purified water.

Add the talc in the triethyl citrate dispersion.

Homogenize the dispersion using a homogenizer.

Add slowly the Eudragit® FS 30D dispersion to the talc/TEC dispersion with stirring.

Continue to stir the coating dispersion until the coating process is complete.

Coating Conditions for the Application of Eudragit FS30D Aqueous Coating Dispersion The following coating parameters were used for coating with each of the Eudragit® FS 30 D aqueous film coating.

| Coating Equipment | STREA 1 ™ Table Top Laboratory Fluid Bed Coater |
|---|---|
| Spray nozzle diameter | 1.2 mm |
| Material Charge | 300 gram |
| Inlet Air Temperature | 38° C. |
| Outlet Air Temperature | 22° C. |
| Atomization Air Pressure | 1.6 Bar |
| Pump Rate | 6 gram per minute |

Coat pellets with Eudragit FS 30D coating dispersion dispersion such that you apply 30% coat weight gain to the pellets.

Encapsulation of the Doxycycline Hyclate Pellets

Pellets are filled into hard gelatin capsules at a ratio of 25%:25%:25%:25% Immediate-Release Pellets (uncoated), Eudragit L30 D-55/Eudragit NE 30D coated pellets 20% weight gain, Eudragit FS 30D/Eudragit L 30 D-55 coated pellets 20% weight gain and Eudragit FS 30D coated pellets respectively. The capsule is filled with the four different pellets to achieve a total dose of 100 mg/capsule or 200 mg/capsule.

The present invention is particularly advantageous in that there is provided an antibiotic product which provides an improvement over twice a day administration of the antibiotic and an improvement over a once a day administration of the antibiotic.

Numerous modification and variations of the present invention are possible in light of the above teachings and therefore, within the scope of the appended claims the invention may be practiced otherwise than as particularly described.

What is claimed is:

1. A once-a-day antibiotic product comprising: first, second, and third dosage forms; each of said dosage forms comprising a tetracycline and a pharmaceutically acceptable carrier; said first dosage form being an immediate release dosage form; said second and third dosage forms being delayed release dosage forms; wherein each of said first, second, and third dosage forms initiates release of the tetracycline at different times; wherein Cmax of the total tetracycline released from said product is achieved in less than about 12 hours from administration; and wherein said once-a-day product contains the total dosage of the tetracycline for a twenty-four hour period.

2. The product of claim 1, wherein said tetracycline is doxycycline.

3. The product of claim 2, wherein the Cmax for the product is reached no earlier than four hours after administration.

4. The product of claim 2, wherein the doxycycline released from the first dosage form reaches a Cmax within from about 0.5 hours to about 2 hours after administration of the product.

5. The product of claim 2, wherein the doxycycline released from the second dosage form reaches a Cmax in no more than about 4 hours after administration of the product.

6. The product of claim 2, wherein the doxycycline released from the third dosage form reaches a Cmax within 8 hours after administration of the product.

7. The product of claim 2, wherein the immediate release dosage form contains at least 20% and no more than 50% of the total dosage of doxycycline.

8. The product of claim 2, wherein the product is an oral dosage form.

9. The product of claim 2, wherein the doxycycline released from the second dosage form reaches a Cmax after Cmax is reached for the doxycycline released from the first dosage form.

10. The product of claim 2, wherein the doxycycline released from the third dosage form reaches a Cmax after Cmax is reached for the doxycycline released from the second dosage form.

11. The product of claim 2, further comprising a fourth dosage form, said fourth dosage form being a delayed release dosage form comprising doxycycline and a pharmaceutically acceptable carrier; and wherein doxycycline released from said fourth dosage form reaches a Cmax after Cmax is achieved for doxycycline released from each of said first, second, and third dosage forms.

12. The product of claim 11, wherein the Cmax for the product is reached no earlier than four hours after administration.

13. The product of claim 11, wherein the doxycycline released from the first dosage form reaches a Cmax within from about 0.5 hours to about 2 hours after administration of the product.

14. The product of claim 11, wherein the doxycycline released from the second dosage form reaches a Cmax in no more than about 4 hours after administration of the product.

15. The product of claim 11, wherein the doxycycline released from the third dosage form reaches a Cmax within 8 hours after administration of the product.

16. The product of claim 11, wherein said second dosage form initiates release of doxycycline before said third dosage form, wherein said third dosage form initiates release of doxycycline before said fourth dosage form, wherein said second dosage form provides 20% to 35% by weight of the total doxycycline released by said second, third, and fourth dosage forms, wherein said third dosage form provides from 20% to 40% by weight of the total doxycycline released by said second, third, and fourth dosage forms, and wherein said fourth dosage form provides the remainder of the total doxycycline released by said second, third, and fourth dosage forms.

17. The product of claim 11, wherein the product is an oral dosage form.

18. The product of claim 11, wherein the doxycycline released from the second dosage form reaches a Cmax after Cmax is reached for the doxycycline released from the first dosage form.

19. The product of claim 11, wherein the doxycycline released from the third dosage form reaches a Cmax after Cmax is reached for the doxycycline released from the second dosage form.

20. A process for treating a bacterial infection in a host comprising:

administering to a host the product of claim 1, once-a-day.

21. A process for treating a bacterial infection in a host comprising:

administering to a host the doxycycline product of claim 2, once-a-day.

22. A process for treating a bacterial infection in a host comprising:

administering to a host the doxycycline product of claim 3, once-a-day.

23. A process for treating a bacterial infection in a host comprising:

administering to a host the doxycycline product of claim 4, once-a-day.

24. A process for treating a bacterial infection in a host comprising:

administering to a host the doxycycline product of claim 5, once-a-day.

25. A process for treating a bacterial infection in a host comprising:

administering to a host the doxycycline product of claim 6, once-a-day.

26. A process for treating a bacterial infection in a host comprising:

administering to a host the doxycycline product of claim 7, once-a-day.

27. A process for treating a bacterial infection in a host comprising:

administering to a host the doxycycline product of claim 8, once-a-day.

28. A process for treating a bacterial infection in a host comprising:

administering to a host the doxycycline product of claim 9, once-a-day.

29. A process for treating a bacterial infection in a host comprising:

administering to a host the doxycycline product of claim 10, once-a-day.

30. A process for treating a bacterial infection in a host comprising:

administering to a host the doxycycline product of claim 11, once-a-day.

31. A process for treating a bacterial infection in a host comprising:

administering to a host the doxycycline product of claim 12, once-a-day.

32. A process for treating a bacterial infection in a host comprising:

administering to a host the doxycycline product of claim 13, once-a-day.

33. A process for treating a bacterial infection in a host comprising:

administering to a host the doxycycline product of claim 14, once-a-day.

34. A process for treating a bacterial infection in a host comprising:

administering to a host the doxycycline product of claim 15, once-a-day.

35. A process for treating a bacterial infection in a host comprising:
   administering to a host the doxycycline product of claim 16, once-a-day.

36. A process for treating a bacterial infection in a host comprising:
   administering to a host the doxycycline product of claim 17, once-a-day.

37. A process for treating a bacterial infection in a host comprising:
   administering to a host the doxycycline product of claim 18, once-a-day.

38. A process for treating a bacterial infection in a host comprising:
   administering to a host the doxycycline product of claim 19, once-a-day.

39. The product of claim 2, wherein the doxycycline is in the form of a salt.

40. A process for treating a bacterial infection in a host comprising:
   administering to a host the doxycycline product of claim 39, once-a-day.

* * * * *

UNITED STATES PATENT AND TRADEMARK OFFICE
CERTIFICATE OF CORRECTION

PATENT NO. : 6,730,320 B2
DATED : May 4, 2004
INVENTOR(S) : Rudnic et al.

It is certified that error appears in the above-identified patent and that said Letters Patent is hereby corrected as shown below:

Colunm 2,
Line 55, after "$C_{max}$" and before "for" delete "a"

Column 6,
Line 43, delete "clarithromycoin" and insert -- clarithromycin --
Line 44, after "penicillin V," and before "salts" delete "peniciliin" and insert
-- penicillin --

Column 9,
Example 26, delete "Eudgragit" and insert -- Eudragit --
Example 29, delete "Eudgragit" and insert -- Eudragit --

Column 10,
Example 38, delete "Eudgragit" and insert -- Eudragit --

Column 20,
Line 62, after "Eudragit®" and before "S 100" delete "claim 11, wherein"

Column 22,
Line 8, delete "dispersim" and insert -- dispersion --

Signed and Sealed this

Twentieth Day of July, 2004

JON W. DUDAS
*Acting Director of the United States Patent and Trademark Office*